(12) United States Patent
Kimoto et al.

(10) Patent No.: US 7,912,434 B2
(45) Date of Patent: Mar. 22, 2011

(54) RECEIVING SYSTEM

(75) Inventors: Seiichiro Kimoto, Hachioji (JP); Manabu Fujita, Hino (JP); Toshiaki Shigemori, Hachioji (JP); Ayako Nagase, Hachioji (JP); Akira Matsui, Hino (JP); Kazutaka Nakatsuchi, Hino (JP)

(73) Assignee: Olympus Corporation, Tokyo (JP)

( * ) Notice: Subject to any disclaimer, the term of this patent is extended or adjusted under 35 U.S.C. 154(b) by 1030 days.

(21) Appl. No.: 11/631,469

(22) PCT Filed: Jun. 23, 2005

(86) PCT No.: PCT/JP2005/011552
§ 371 (c)(1),
(2), (4) Date: Feb. 26, 2007

(87) PCT Pub. No.: WO2006/003838
PCT Pub. Date: Jan. 12, 2006

(65) Prior Publication Data
US 2007/0249285 A1    Oct. 25, 2007

(30) Foreign Application Priority Data

Jun. 30, 2004    (JP) .................................. 2004-194887

(51) Int. Cl.
*H04B 1/06* (2006.01)
(52) U.S. Cl. .................... 455/272; 455/13.3; 455/562.1; 455/575.7; 455/269; 455/274; 343/702; 600/300
(58) Field of Classification Search .................. 455/41.2
See application file for complete search history.

(56) References Cited

U.S. PATENT DOCUMENTS

| 3,641,439 | A | * | 2/1972 | Aslan | 343/703 |
| 3,921,621 | A | * | 11/1975 | Baessler | 600/549 |
| 5,604,531 | A | | 2/1997 | Iddan et al. | |
| 7,295,226 | B1 | * | 11/2007 | Meron et al. | 348/77 |
| 7,596,359 | B2 | * | 9/2009 | Kimoto et al. | 455/137 |
| 2003/0023150 | A1 | * | 1/2003 | Yokoi et al. | 600/300 |
| 2007/0018895 | A1 | * | 1/2007 | Bolin | 343/702 |

FOREIGN PATENT DOCUMENTS

| JP | 2000-307492 | 11/2000 |
| JP | 2001-196951 | 7/2001 |
| JP | 2003-19111 | 1/2003 |
| JP | 2003-209499 | 7/2003 |
| JP | 2003-523795 | 8/2003 |
| JP | 2004-483361 | 2/2004 |
| WO | WO2001/35813 | 5/2001 |

* cited by examiner

*Primary Examiner* — Zhiyu Lu
(74) *Attorney, Agent, or Firm* — Scully, Scott, Murphy & Presser, P.C.

(57) ABSTRACT

To realize a receiving system that can excellently receive radio signals before and after a body insertable device, which is a radio signal source, is inserted into a subject, the receiving system has a first receiving antenna (1), a second receiving antenna (2), and a receiving apparatus (3). The first receiving antenna (1) is used when the body insertable device is outside the subject. The second receiving antenna (2) is used when the body insertable device is inserted into the subject. The receiving apparatus (3) performs a receiving processing on radio signals received through the first receiving antenna (1) or the second receiving antenna (2). In the receiving system, a receiving antenna connected to an antenna connector (13) provided in the receiving apparatus (3) is switched between the first receiving antenna (1) and the second receiving antenna (2) corresponding to a difference in propagation states of radio signals transmitted from the body insertable device before and after the body insertable device is inserted into the subject. Consequently, the receiving system that can excellently receive the radio signals before and after the body insertable device is inserted into the subject is realized.

8 Claims, 7 Drawing Sheets

RECEIVING SYSTEM

TECHNICAL FIELD

The present invention relates to a technique for receiving radio signals transmitted from a body insertable device, which is to be inserted into a subject.

BACKGROUND ART

Recently, a swallowable capsule endoscope has been proposed in a field of endoscopes. The capsule endoscope has an imaging function and a radio transmission function. The capsule endoscope travels through inside a body cavity, e.g., through inside organs such as a stomach and a small intestine, during a period from when the capsule endoscope is inserted from a mouth of a subject for an observation (examination) until when the capsule endoscope is naturally discharged, while following peristaltic motion of the organs. Then, as the capsule endoscope travels through inside the organs, the capsule endoscope obtains an image inside the subject for, for example, every 0.5 second.

While the capsule endoscope travels through inside the body cavity, image data obtained inside the body by the capsule endoscope are sequentially transmitted to outside by radio transmission, and stored in a memory provided outside. Since the subject carries around a receiving apparatus having the radio transmission function and a memory function, the subject can freely move during the period from when the capsule endoscope is swallowed until when the capsule endoscope is discharged. After the capsule endoscope is discharged, the image of the organs is displayed on a display based on the image data stored in the memory, so that a doctor or a nurse can make diagnosis (for example, see Patent Document 1).

A viewer device that performs a test and a real time observation is proposed. The test determines whether the capsule endoscope operates normally, and the real time observation is performed on the image data acquired by the capsule endoscope inserted into the subject. Specifically, unlike the aforementioned receiving apparatus, the viewer device does not have a storage unit such as a memory; however, the viewer device does have a display that displays the image data extracted from the received radio signals. By the use of the viewer device, malfunction of the capsule endoscope to be used can be recognized before the capsule endoscope is inserted into the subject of a patient and the like, and the real time observation can be performed on a content of the transmitted image data after the capsule endoscope is inserted into the subject.

Patent Document 1: Japanese Patent Application Laid-open No. 2003-19111

DISCLOSURE OF INVENTION

Problem to be Solved by the Invention

The conventional viewer device used for the capsule endoscope performs the performance test on the capsule endoscope before the capsule endoscope is inserted into the subject, and performs the observation on the image data after the capsule endoscope is inserted into the subject. However, the viewer device cannot adequately be used to perform each of the performance test and the observation on the image data, and the viewer device has an insufficient function to perform each of the performance test and the observation on the image data.

The conventional viewer device performs a receiving processing on the radio signals before and after the capsule endoscope is inserted into the subject, by a single configuration. Hence, although strength of the radio signals transmitted from the capsule endoscope, a position of the viewer device appropriate for receiving the radio signals, and the like are different before and after the capsule endoscope is inserted into the subject, it is difficult to realize a viewer device corresponding to the differences.

The present invention is provided in view of the foregoing, and in a receiving system that receives radio signals transmitted from a body insertable device such as an capsule endoscope, it is an object of the present invention to provide the receiving system that has excellent operability and can excellently receive the radio signals before and after the body insertable device is inserted into the subject.

Means for Solving Problem

A receiving system according to one aspect of the present invention receives a radio signal transmitted from a body insertable device which is to be inserted into a subject. The receiving system also includes a first receiving antenna configured to be appropriate for receiving the radio signal transmitted from the body insertable device when the body insertable device is outside the subject, a second receiving antenna configured to be appropriate for receiving the radio signal transmitted from the body insertable device when the body insertable device is inside the subject, and a receiving apparatus that includes at least a receiving circuit performing a predetermined receiving processing on the radio signal received through one of the first receiving antenna and the second receiving antenna.

According to the receiving system, the first receiving antenna and the second receiving antenna, which are to be connected to the receiving apparatus, are switched before and after the body insertable device is inserted into the subject, based on a difference in propagation states of the radio signals transmitted from the body insertable device. Consequently, a receiving system that can excellently receive the radio signals before and after the body insertable device is inserted into the subject can be realized.

In the receiving system, the receiving apparatus further may include an antenna connector that is electrically connected to the receiving circuit, and allow one of the first receiving antenna and the second receiving antenna to be connected to the receiving apparatus.

In the receiving system, the receiving apparatus may further include a case member that houses the receiving circuit and the first receiving antenna; an antenna connector from which the second receiving antenna is detachable; and a selector that selects one of the first receiving antenna and the second receiving antenna, and outputs the radio signal received through the antenna selected to the receiving circuit.

In the receiving system, the selector may select the antenna based on a strength of the radio signal received through the first receiving antenna and the second receiving antenna.

The receiving system may further include a connection detector that determines whether the second receiving antenna and the antenna connector are connected to each other. The selector may select the first receiving antenna when the connection detector determines that the second receiving antenna and the antenna connector are disconnected from each other, and select the second receiving antenna when the connection detector determines that the second receiving antenna and the antenna connector are connected to each other.

In the receiving system, the first receiving antenna may have a member with a predetermined rigidity, and the second receiving antenna may have a member that is deformable according to an external force.

In the receiving system, the first receiving antenna may have a rod-like member having a helical configuration, and the second receiving antenna may have a loop antenna and a cable extended from the loop antenna.

The receiving system according to may further include a signal processor that extracts subject interior information from a signal including the subject interior information which is transmitted from the body insertable device and processed by the receiving circuit, and a display unit that displays a content of the subject interior information extracted by the signal processor.

EFFECT OF THE INVENTION

A receiving system according to the present invention switches a receiving antenna, which is to be connected to a receiving apparatus, between a first receiving antenna and a second receiving antenna before and after the body insertable device is inserted into a subject, corresponding to a difference in propagation states of radio signals transmitted from a body insertable device. Consequently, the receiving system that can excellently receive the radio signals before and after the body insertable device is inserted into the subject can be realized.

EXPLANATIONS OF LETTERS OR NUMERALS

Figure 1:
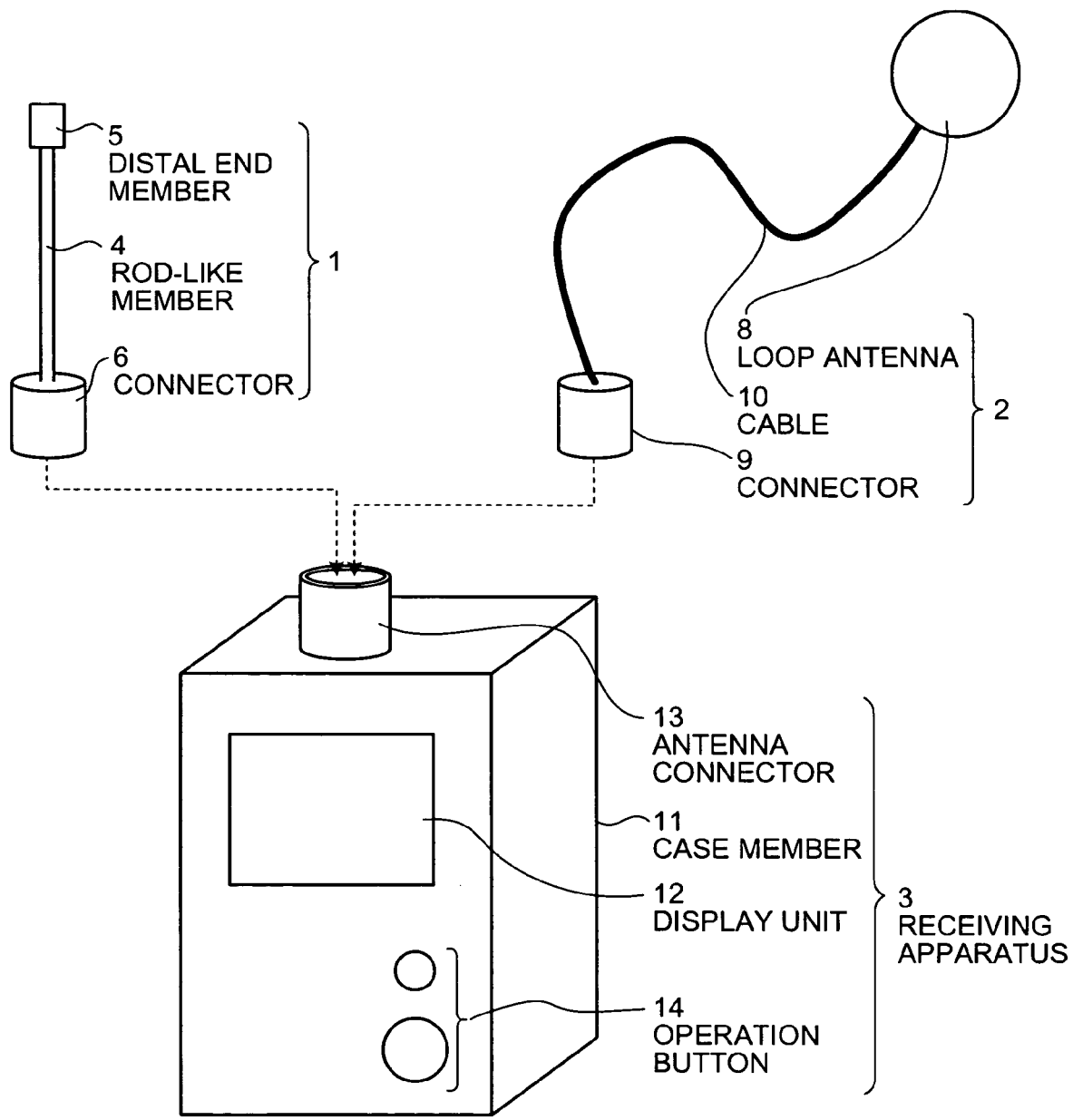
FIG. 1 is a schematic diagram of an overall structure of a receiving system according to a first embodiment.

1 First receiving antenna
2 Second receiving antenna
3 Receiving apparatus
4 Rod-like member
5 Distal end member
6 Connector
8 Loop antenna
9 Connector
10 Cable
11 Case member
12 Display
13 Antenna connector
14 Operation button
16 Receiving circuit
17 Signal processor
18 Controller
19 Power supply unit
21 Capsule endoscope
22 Subject
24 First receiving antenna
25 Receiving apparatus
27 Selector
28 Receiving circuit
29 Strength comparator
30 Receiving apparatus
31 Selector
32 Connection detector

BEST MODE(S) FOR CARRYING OUT THE INVENTION

Exemplary embodiments of a receiving system according to the present invention will be described below. It should be noted that the accompanying drawings are merely schematic, and relation between width and thickness of each portion, thickness ratio of one portion to another, and the like may be different in an actual apparatus and a system. The dimensional relations and the ratio may be different from one drawing to another.

First Embodiment

A receiving system according to a first embodiment is explained. FIG. 1 is a schematic diagram of an overall structure of the receiving system according to the first embodiment. As shown in FIG. 1, the receiving system according to the first embodiment has a first receiving antenna 1, a second receiving antenna 2, and a receiving apparatus 3. Each of the first receiving antenna 1 and the second receiving antenna 2 is used to receive radio signals under a predetermined circumstance. The receiving apparatus 3 receives the radio signals through the first receiving antenna 1 or the second receiving antenna 2, performs a predetermined processing on the received radio signals, and displays information contained in the radio signals.

The first receiving antenna 1 is configured appropriately for receiving the radio signals while the capsule endoscope that sends the radio signals is outside the subject. The first receiving antenna 1 is formed with, for example, a helical antenna. Specifically, the first receiving antenna 1 has a rod-like member 4 having predetermined rigidity, a distal end member 5 formed at one end of the rod-like member 4, and a connector 6 formed at other end of the rod-like member 4. The rod-like member 4 is used to wind a metal wire (not shown) having a predetermined helical configuration therearound.

The rod-like member 4 is used as a supporting body for the aforementioned metal wire that functions as an antenna portion of the first receiving antenna 1. Specifically, the metal wire is helically wound around the rod-like member 4 to form the antenna portion of the first receiving antenna 1. In an example shown in FIG. 1, the rod-like member 4 is formed with a single rod-like body. However, the rod-like member 4 is not limited thereto, and a rod-like body having any configuration such as a configuration with a foldable shape may be used, as long as the rod-like body functions as the supporting body. As described hereinafter, since portability of the first receiving antenna 1 is stressed to determine the configuration of the first receiving antenna 1, it is preferred to associate the portability with the configuration of the first receiving antenna 1.

The connector 6 serves to connect the first receiving antenna 1 to the receiving apparatus 3, when the first receiving antenna 1 is used. Specifically, the shape of the connector 6 is determined so that, for example, the connector 6 fits into an antenna connector 13 (described later) provided on the receiving apparatus 3, and the connector 6 electrically connects the antenna portion provided in the first receiving antenna 1 and a circuit mechanism inside the receiving apparatus 3. The connector 6 is preferred to have an electronic configuration for matching impedance of when the connector 6 is connected to the antenna connector 13.

The second receiving antenna 2 is configured appropriately for receiving the radio signals while the capsule endoscope that sends the radio signals is inside the subject. Specifically, the second receiving antenna 2 has a loop antenna 8 that functions as an antenna portion, a connector 9 for connecting the second receiving antenna 2 and the receiving apparatus 3 when the second receiving antenna 2 is used, and a cable 10 that electrically connects the loop antenna 8 and the connector 9.

The loop antenna 8 serves to receive the radio signals, which are transmitted from the capsule endoscope and penetrate through body tissue of the subject. Specifically, the loop antenna 8 is formed by a wiring configuration in which a wiring is formed spirally on a film-like substrate. When the loop antenna 8 is fixed on a body surface of the subject during use as described hereinafter, it is preferred to apply bonding agent or the like on a back side of the film-like substrate. As described hereinafter, the second receiving antenna 2 is preferred to have a configuration stressing receiving sensitivity thereof. Hence, the loop antenna 8 is preferred to have a configuration in which high receiving sensitivity can be obtained.

The connector 9 serves to electrically connect the antenna connector 13 provided on the receiving apparatus 3 and the loop antenna 8. Specifically, as similar to the connector 6 provided in the first receiving antenna 1, the connector 9 has a shape determined so that, for example, the connector 9 fits into the antenna connector 13, and preferably, the connector 9 has a configuration for matching impedance between the connector 9 and the antenna connector 13.

The cable 10 serves to electrically connect the loop antenna 8 and the connector 9. Specifically, the cable 10 has a configuration in which an electrically conductive wiring is covered by an insulated member, and the cable 10 can easily be deformed due to external force. When the second receiving antenna 2 is used as described hereinafter, it is required to frequently adjust a position of the loop antenna 8 in accordance with a position of the capsule endoscope inside the subject. Hence, from a perspective of adjusting the position of the loop antenna 8 without moving the receiving apparatus 3, the cable 10 having flexibility electrically connects the loop antenna 8 and the connector 9.

The receiving apparatus 3 is explained. As shown in FIG. 1, the receiving apparatus 3 has a case member 11 in which a predetermined electronic circuit and the like are housed, a display unit 12, the antenna connector 13, and an operation button 14. The display unit 12, the antenna connector 13, and the operation button 14 are each arranged in each opening and the like formed on the case member 11.

The case member 11 serves to house the electronic circuit performing a receiving processing and the like thereinside. Specifically, the case member 11 is formed with a plastic member and the like having a predetermined physical strength, and has the openings for arranging the display unit 12 and the like therein. To prevent noise radio waves generated by the electronic circuit provided inside the case member 11 from leaking out, and to prevent the noise radio waves outside the case member 11 from entering into the case member 11, it is preferred to coat the interior face of the case member 11 with electrically conductive material.

The display unit 12 serves to display a content of the radio signals, which are transmitted from the capsule endoscope and received through one of the first receiving antenna 1 and the second receiving antenna 2. The display unit 12 is normally formed with a small display panel such as a liquid crystal panel. However, the display unit 12 is not limited thereto, and any configuration may be used as long as the content of the radio signals can be displayed. Specifically, a configuration that displays the content on other medium such as a printer can be used as the display unit 12 rather than using the liquid crystal display and the like to directly display the content of the radio signals, and a configuration that, for example, vocally displays the content can be used as the display unit 12 rather than using a configuration that visually displays the content. The content of the radio signals displayed on the display unit 12 can be an image, or can be textual information.

The antenna connector 13 serves to connect the first receiving antenna 1 or the second receiving antenna 2 to the receiving apparatus 3. Specifically, the antenna connector 13 houses each of the connector 6 and the connector 9 while electrically connecting the connector 6 or the connector 9 to the rod-like member 4 and the loop antenna 8. Further, the antenna connector 13 is electrically connected to the electrical circuit and the like inside the case member 11. The antenna connector 13 is connected to each of the connector 6 and the connector 9 in one-to-one relationship, and the antenna connector 13 cannot be connected to both of the connector 6 and the connector 9 simultaneously.

Figure 2:
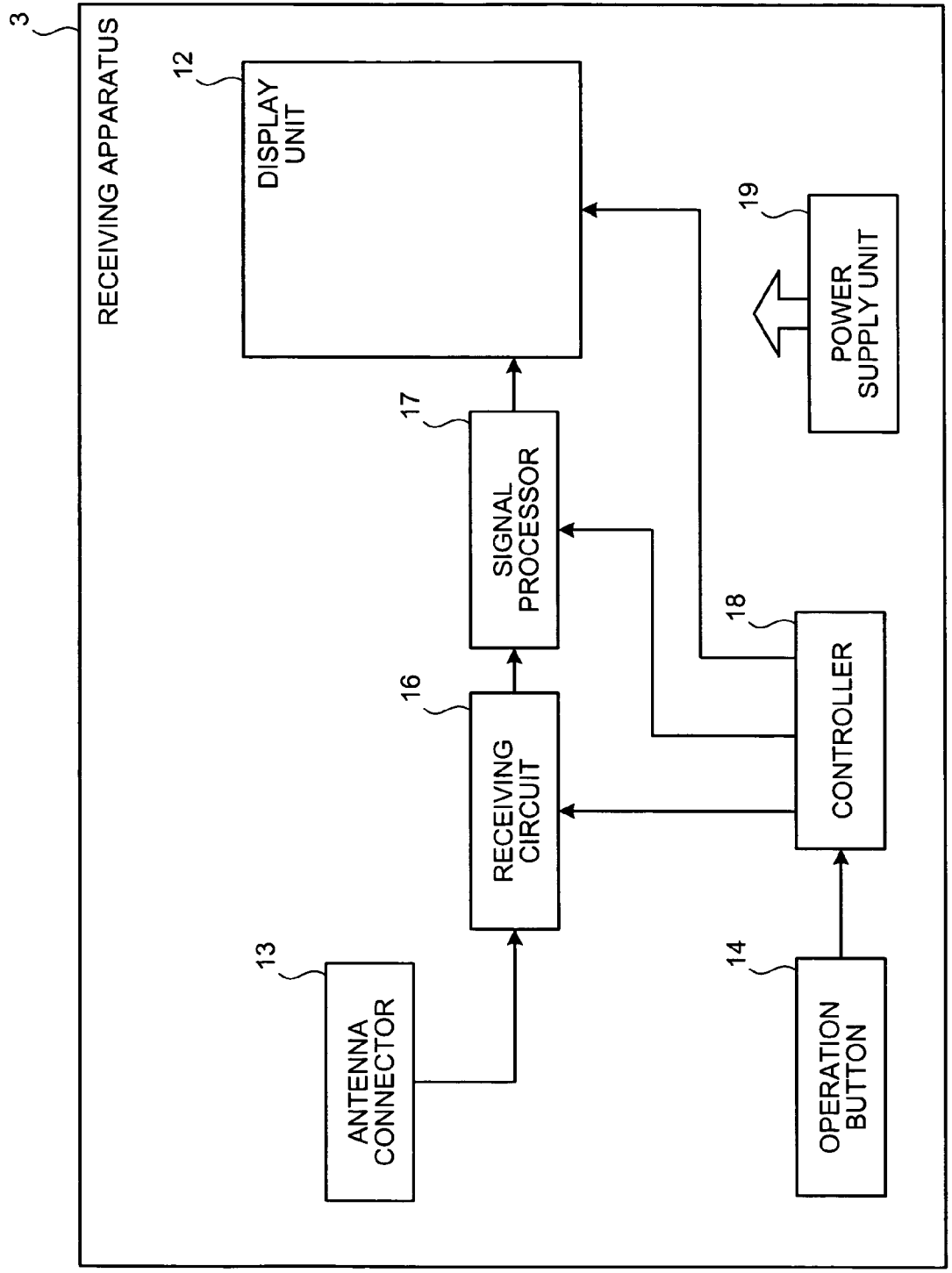
FIG. 2 is a block diagram of a structure of a receiving apparatus provided in the receiving system according to the first embodiment.

Elements arranged inside the case member 11 are explained. FIG. 2 is a schematic block diagram of an overall structure of the receiving apparatus 3 including the elements provided inside the case member 11. As shown in FIG. 2, the receiving apparatus 3 has a receiving circuit 16, a signal processor 17, a controller 18, and a power supply unit 19. The receiving circuit 16 performs a predetermined receiving processing on the radio signals input through the antenna connector 13. The signal processor 17 performs a modulation and the like on signals output from the receiving circuit 16. The controller 18 controls driven states and the like of the receiving circuit 16, the signal processor 17, and the display unit 12 based on information input through the operation button 14. The power supply unit 19 supplies driving power to each element. Since the receiving apparatus 3 has the aforementioned configuration, when image data is transmitted from the capsule endoscope, for example, the receiving circuit 16 performs the receiving processing on the radio signals input through the antenna connector 13, the signal processor 17 extracts the image data, and the display unit 12 displays the extracted image data.

Application and usage of the receiving system according to the first embodiment is explained below. Hereinafter, one application of the receiving system in which the first receiving antenna 1 is connected to the antenna connector 13 and other application of the receiving system in which the second receiving antenna 2 is connected to the antenna connector 13 are each explained.

Figure 3:
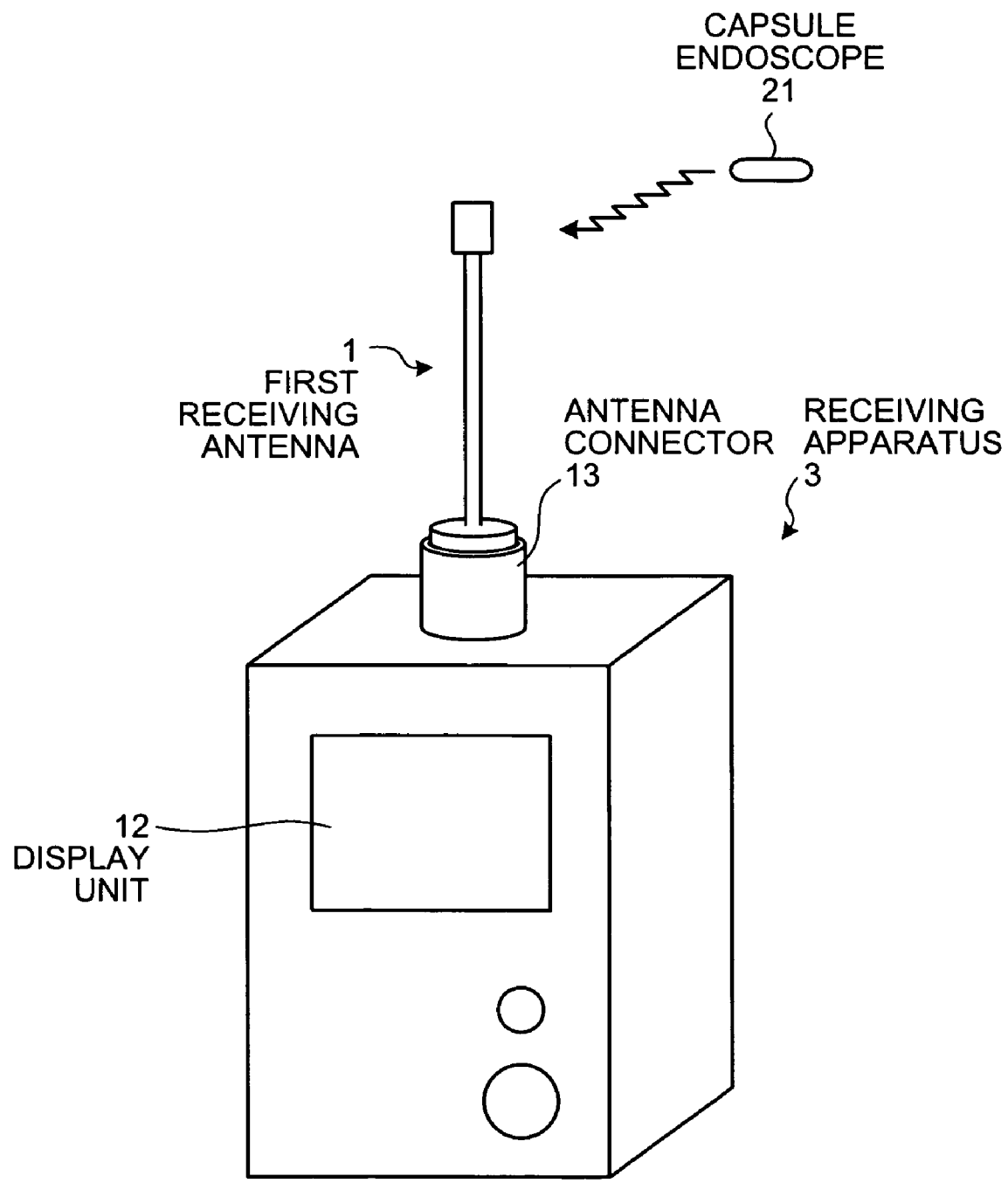
FIG. 3 is a schematic diagram showing how the receiving system is utilized prior to an introduction of an capsule endoscope into a subject.

FIG. 3 is a schematic diagram showing how the receiving system is used when the first receiving antenna 1 is used. As shown in FIG. 3, when the capsule endoscope 21 is outside the subject, the receiving system according to the first embodiment is used with the first receiving antenna 1 connected to the antenna connector 13, as an antenna unit.

When the capsule endoscope 21 is outside the subject, e.g., right before the capsule endoscope 21 is inserted into the subject, the first receiving antenna 1 is used to determine whether the capsule endoscope 21 operates normally. Specifically, a doctor, a nurse, and the like who test the capsule endoscope 21 hold the capsule endoscope 21, and arrange the first receiving antenna 1 near the capsule endoscope 21 as shown in FIG. 3. Then, the doctor, the nurse, and the like press a predetermined operation button 14 to drive the receiving apparatus 3. The receiving apparatus 3 receives the radio signals transmitted from the capsule endoscope 21 through the first receiving antenna 1, performs the predetermined processing on the received radio signals, and displays the content of the radio signals on the display unit 12. Then, the doctor and the like determine whether the capsule endoscope 21 operates normally based on the content displayed on the display unit 12, and decide whether to insert the capsule endoscope 21 into the subject. Specifically, for example, the doctor or the like decides not to use the capsule endoscope 21 when definition of the image displayed on the display unit 12 is less than an acceptable level, whereas the doctor or the like decides that the capsule endoscope 21 operates normally when the definition of the image is greater than or equal to the acceptable level, and inserts the tested capsule endoscope 21 into the subject.

When the aforementioned test is performed, the doctor, the nurse, and the like who test the capsule endoscope 21 can perform the test while visually recognizing the capsule endoscope 21, and there is nothing preventing the radio signals from propagating between the capsule endoscope 21 and the first receiving antenna 1. Therefore, the doctor and the like can easily arrange the receiving system at a position appropriate for receiving the radio signals, and the radio signals transmitted from the capsule endoscope 21 can be received at high sensitivity by the arrangement of the receiving system at the appropriate position. Hence, the receiving sensitivity of the first receiving antenna 1 is not particularly stressed in the first embodiment, and the portability described hereinafter of the receiving system is stressed.

Figure 4:
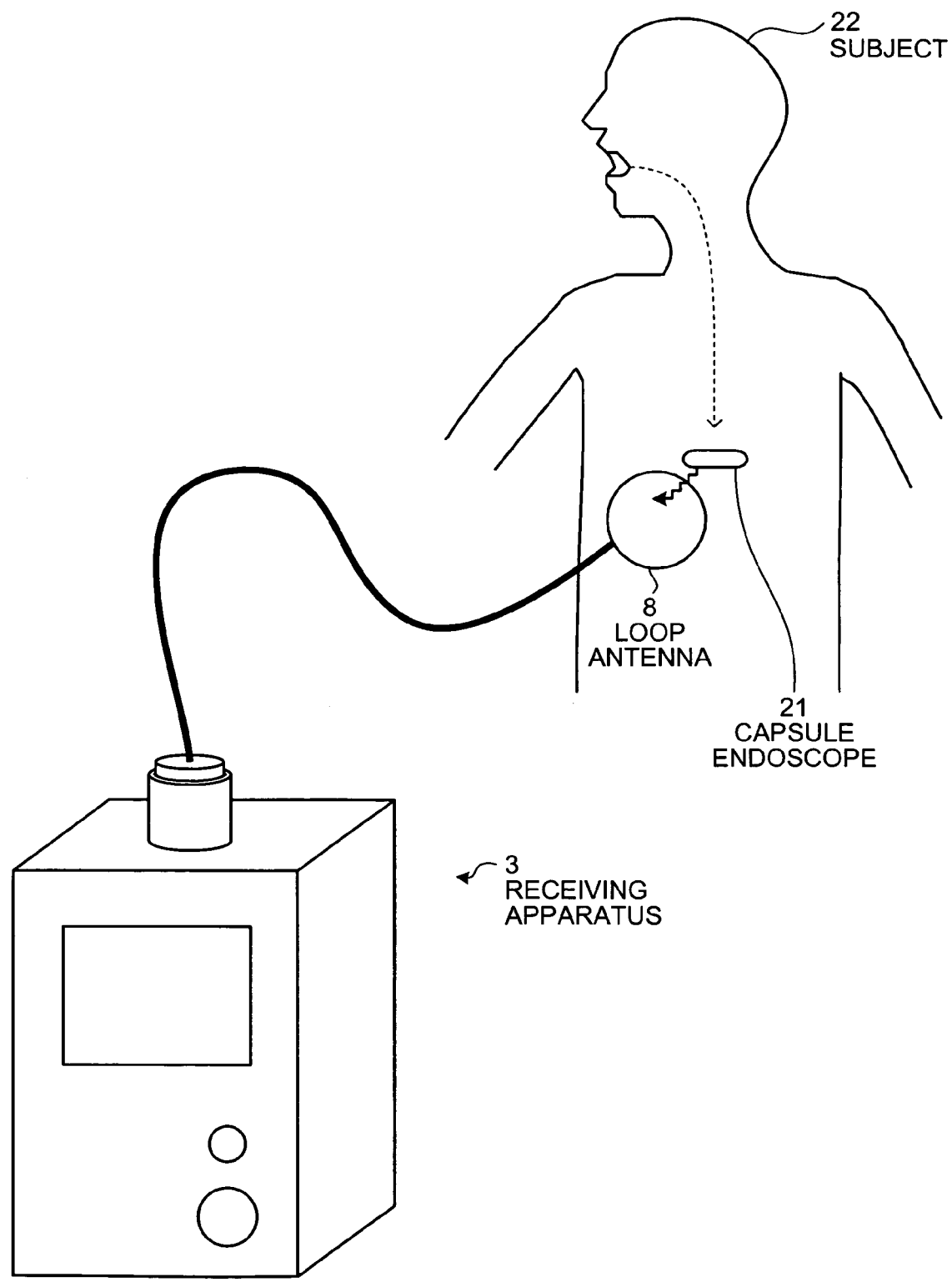
FIG. 4 is a schematic diagram showing how the receiving system is utilized after the introduction of the capsule endoscope into the subject.

The receiving system of when the second receiving antenna 2 is used is explained. FIG. 4 is a schematic diagram showing how the receiving system is used when the second receiving antenna 2 is connected to the antenna connector 13 provided on the receiving apparatus 3.

The receiving system is used as shown in FIG. 4, when, for example, the content of the subject interior image obtained by the capsule endoscope 21 is observed in real time after the capsule endoscope 21 is inserted into the subject 22. When the content of the subject interior image is observed in real time, the capsule endoscope 21 is inside the subject 22. Hence, unlike when the first receiving antenna 1 is connected to the antenna connector 13 as shown in FIG. 3, it is difficult for the operator of the receiving system to determine the position of the capsule endoscope 21. Therefore, when the content of the subject interior image is observed in real time as shown in FIG. 4, the operator of the receiving system, while checking the content displayed on the display unit 12, changes the position of the second receiving antenna 2 with which the radio signals are received, and particularly, changes the position of the loop antenna 8 provided in the second receiving antenna 2 to adjust the position and an orientation direction of the loop antenna 8 so as to optimize the receiving condition of the radio signals transmitted from the capsule endoscope 21. Then, the operator such as the doctor observes the subject interior image displayed on the display unit 12 in real time while arranging the loop antenna 8 at an optimal position for receiving the radio signals, and make diagnosis when necessary.

Advantages associated with the receiving system according to the first embodiment is explained. In the receiving system according to the first embodiment, the receiving function that excellently receives the radio signals transmitted from the body insertable device, such as the capsule endoscope 21, before and after the body insertable device is inserted into the subject can be realized at low cost.

As shown in FIGS. 3 and 4, the receiving system having the function of receiving the radio signals transmitted from the body insertable device such as the capsule endoscope 21 performs the receiving operation on the radio signals under the different conditions, i.e., before and after the body insertable device is inserted into the subject. Therefore, when the receiving system with a single configuration is used to perform the receiving operation under the different conditions, it is difficult to perform the receiving operation appropriately for each condition. However, from a perspective of a cost of usage and the like, it is not preferred to use plural independent receiving systems, each for one condition.

Generally, the radio signals transmitted from the body insertable device propagate in different manner before and after the body insertable device is inserted into the subject. Before the body insertable device is inserted into the subject, the body insertable device can be easily placed at any position relative to the receiving antenna, and there exists no material, which affects the propagation state of the radio signals, between the body insertable device and the receiving antenna. On the other hand, after the body insertable device is inserted into the subject, it is difficult to determine the position of the body insertable device inside the subject, and in addition, the radio signals transmitted from the body insertable device always penetrate through the body tissue of the subject before reaching the receiving antenna. Hence, once the body insertable device is inserted into the subject, it becomes necessary to adjust the position and the orientation direction of the receiving antenna by guess, dissimilar to the procedure prior to the insertion.

The radio signals to be received are transmitted from the same body insertable device before and after the body insertable device is inserted into the subject. Hence, frequencies of the transmitted radio signals are the same before and after the capsule endoscope 21 is inserted into the subject 22, and a property of the subject interior information contained in the radio signals does not change. Since the operator of the receiving system observes the content displayed on the display unit 12 to test whether the capsule endoscope 21 operates normally before the capsule endoscope 21 is inserted into the subject 22, and to perform the observation and the like on the content of the subject interior image in real time after the capsule endoscope 21 is inserted into the subject 22, the processing on the received radio signals are the same before and after the capsule endoscope 21 is inserted into the subject 22. Therefore, a same mechanism is used to process the received radio signals before and after the capsule endoscope 21 is inserted into the subject 22.

In view of the foregoing, in the receiving system that receives the radio signals transmitted from the body insertable device, it is not required to use different receiving systems before and after the body insertable device is inserted into the subject, and the common mechanism for processing the radio signals can be used. Hence, the receiving system according to the first embodiment utilizes the same receiving apparatus 3 before and after the body insertable device is inserted into the subject, and the receiving antenna is switched between the first receiving antenna 1 and the second receiving antenna 2 corresponding to the difference in the propagation states of the radio signals before and after the body insertable device is inserted into the subject. Thus, the receiving system according to the first embodiment employing the above mentioned configuration in which the single receiving apparatus 3 is provided is advantageous in that increase in manufacturing cost of the receiving system can be suppressed and that the favorable receiving operation can be performed by accommodating the difference in the propagation states of the radio signals before and after the body insertable device is inserted into the subject using different antennas, i.e., the first receiving antenna 1 and the second receiving antenna 2.

In the receiving system according to the first embodiment, the receiving apparatus 3 has the antenna connector 13 that can be connected to one of the first receiving antenna 1 and the second receiving antenna 2. By the receiving system employing the aforementioned configuration, it is not required to provide an antenna switching mechanism in the receiving apparatus 3; therefore, the configuration of the receiving apparatus 3 can be simplified. In the receiving system according to the first embodiment, the employed receiving antenna is changed by the operator who attaches one of the first receiving antenna 1 and the second receiving antenna 2 to the antenna connector 13, so that a mechanism switching the receiving antennas can be removed. Therefore, in the receiving system according to the first embodiment, the configuration of the receiving apparatus 3 can be simplified.

The antenna connector 13 can be connected to one of the first receiving antenna 1 and the second receiving antenna 2; therefore, the operability of the receiving system is improved. In a receiving system in which the first receiving antenna 1 and the second receiving antenna 2 are both connected to the receiving apparatus 3 at any time, the presence of the second receiving antenna obstructs the operation of the receiving system before, for example, the body insertable device is inserted into the subject, and the first receiving antenna obstructs the operation of the receiving system after the body insertable device is inserted into the subject. On the other hand, in the receiving system according to the first embodiment, the antenna connector 13 can be connected to one of the first receiving antenna 1 and the second receiving antenna 2. Therefore, in the receiving system according to the first embodiment, unused receiving antenna is not connected to the receiving apparatus 3, so that the receiving antenna, which is not used to receive the radio signals, does not hinder the operation of the receiving system.

As described hereinbefore, in the receiving system according to the first embodiment, the first receiving antenna 1 has the rod-like member 4 having the predetermined rigidity. Hence, the receiving system can be easily operated during the test on the body insertable device before the body insertable device is inserted into the subject. Hereinafter, the advantage is explained.

Before the body insertable device is inserted into the subject, the operator of the receiving system can visually recognize the position of the body insertable device, and there is no material preventing the propagation of the radio signals. Therefore, it is not necessary to fumble around to make a subtle adjustment of the position and the like of the receiving antenna for the reception of the radio signals transmitted from the body insertable device; and from a perspective of adjusting the receiving state, it is not required to particularly contrive the configuration of the first receiving antenna 1.

On the other hand, the test must be performed quickly. During the test before the body insertable device is inserted into the subject, the body insertable device performs the imaging operation and the transmission operation on the radio signals, as similar to when the body insertable device is inserted into the subject; therefore, an operating time that is not required to obtain the subject interior information increases as a time required for the test increases, so that power consumption increases by the increased operating time. Hence, the first receiving antenna 1 is preferred to have good operability for the operator to allow the quick test.

In the first embodiment, the first receiving antenna 1 that is to be connected to the receiving apparatus 3 consists of the electrically conductive member having the predetermined rigidity. Hence, by the operator holding the receiving apparatus 3, the position of the first antenna 1 can be determined automatically. Since the position and the orientation direction of the first receiving antenna 1 change in accordance with the receiving apparatus 3, the operator can determine the position and the orientation direction of the first receiving antenna 1 while holding the receiving apparatus 3. Therefore, the receiving system according to the first embodiment has the good operability when the first receiving antenna 1 is connected to the receiving apparatus 3, and the quick test on the body insertable device outside the subject can be performed.

Specifically during the test, the operator generally performs the test by holding the body insertable device in one hand and holding the receiving system in other hand. When the operator holds the receiving system according to the first embodiment to perform the test, the operator can determine the position and the orientation direction of both the receiving apparatus 3 and the first receiving antenna 1 by holding only the receiving apparatus 3 in one hand. Thus, the operator can easily hold the receiving system, the operability improves, and the test can be performed quickly.

In the receiving system according to the first embodiment, the second receiving antenna 2 has the configuration in which the cable 10 having flexibility connects the loop antenna 8 and the connector 9. With such configuration, the operability and the receiving sensitivity of the receiving system after the body insertable device is inserted into the subject improve.

After the body insertable device is inserted into the subject, it is difficult for the operator of the receiving system to determine the position of the body insertable device inside the subject. Hence, to receive the radio signals in a good condition, it is required to fumble around to adjust the position and the orientation direction of the second receiving antenna 2 while confirming the content displayed on the display unit 12. In the first embodiment, even when the second receiving antenna 2 and the receiving apparatus 3 are connected to each other through the connector 9, the loop antenna 8 that functions as the antenna can be moved independently of the receiving apparatus 3 due to the effect of the cable 10. Therefore, while keeping the receiving apparatus 3 at a fixed position, the operator of the receiving system can make fine adjustment of the position and the orientation direction of the loop antenna 8 so as to improve the receiving sensitivity. Thus, the operator can easily perform the operation for the adjustment of the sensitivity while confirming the content displayed on the display unit 12 provided in the receiving apparatus 3.

Specifically, when the operator used the receiving system while keeping the second receiving antenna 2 connected to the antenna connector 13, the operator does not need to hold the body insertable device since the body insertable is in the subject. Therefore, when the operator employs the receiving system according to the first embodiment, the operator can make fine adjustment of the position and the orientation direction of the loop antenna 8 easily by holding the receiving apparatus 3 in one hand and holding the loop antenna 8 provided in the second receiving antenna 2 in other hand. Consequently, the operability can be improved, and the radio signals can be received at high sensitivity.

Second Embodiment

A receiving system according to a second embodiment is explained. The receiving system according to the second embodiment has a configuration in which a first receiving antenna is housed in a receiving apparatus. Hereinafter, the receiving system according to the second embodiment is explained.

Figure 5:
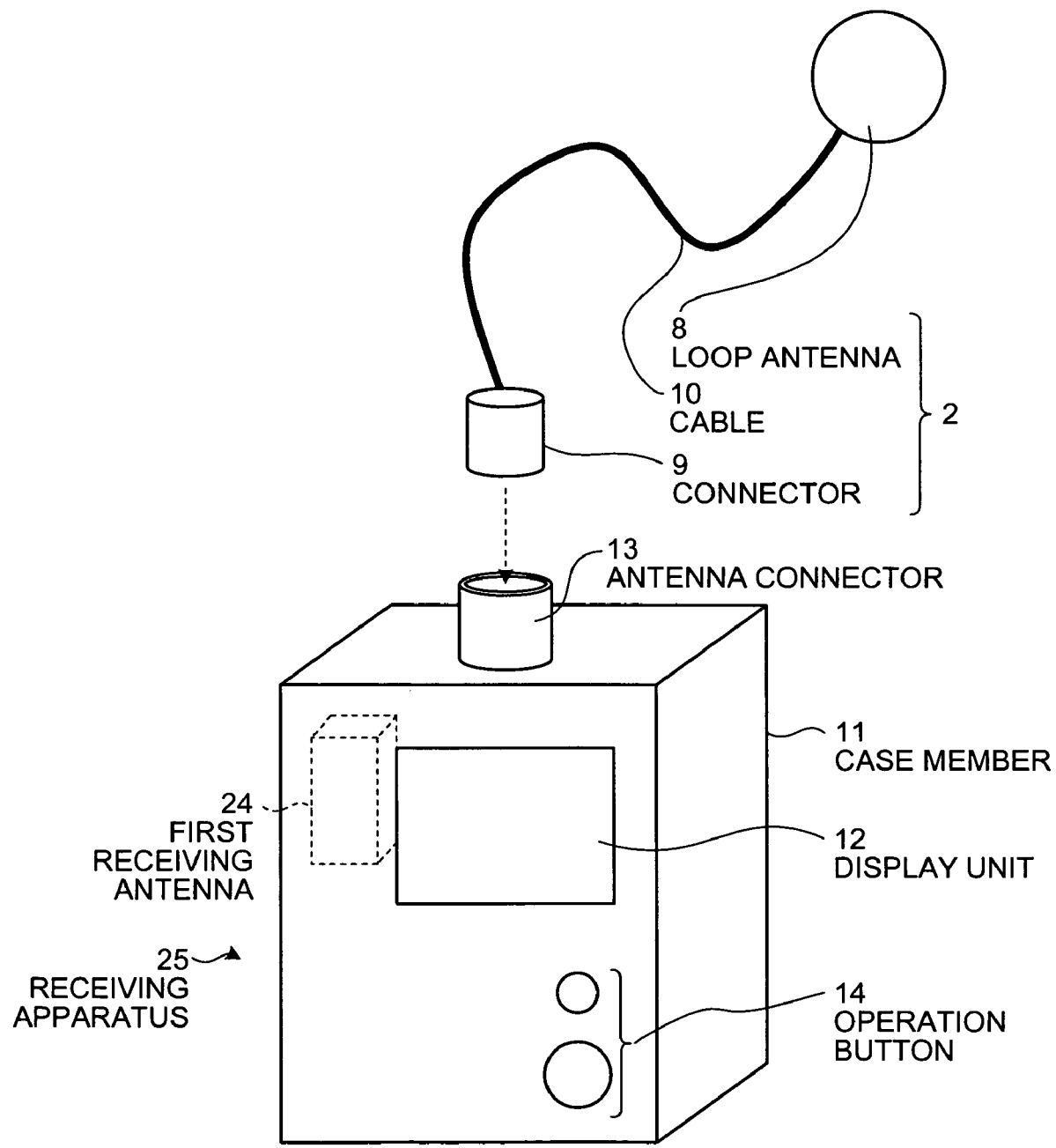
FIG. 5 is a schematic diagram of an over all structure of a receiving system according to a second embodiment.

FIG. 5 is a schematic diagram of an overall configuration of the receiving system according to the second embodiment. As shown in FIG. 5, the receiving system according to the second embodiment has the second receiving antenna 2 having a configuration similar to the configuration of the second receiving antenna of the first embodiment, and a receiving apparatus 25 in which the first receiving antenna 24 is housed. In the second embodiment, elements represented by names, letters, and numerals that are similar to those of the first embodiment have configurations and functions similar to those of the first embodiment as long as not specifically mentioned hereinafter.

As shown in FIG. 5, the receiving apparatus 25 has the case member 11, the display unit 12, the antenna connector 13, and the operation button 14 as similar to the receiving apparatus 3 in the first embodiment, and in addition, the receiving apparatus 25 houses the first receiving antenna 24. Since the receiving apparatus 25 houses the first receiving antenna 24, the configuration inside the case member 11 has additional elements that are different from the elements of the first embodiment. As similar to the first embodiment, the antenna connector 13 provided on the receiving apparatus 25 can house the connector 9, and after the body insertable device such as the capsule endoscope 21 is inserted into the subject, the antenna connector 13 is connected to the second receiving antenna 2, and the antenna connector 13 receives the radio signals received through the second receiving antenna 2.

Figure 6:
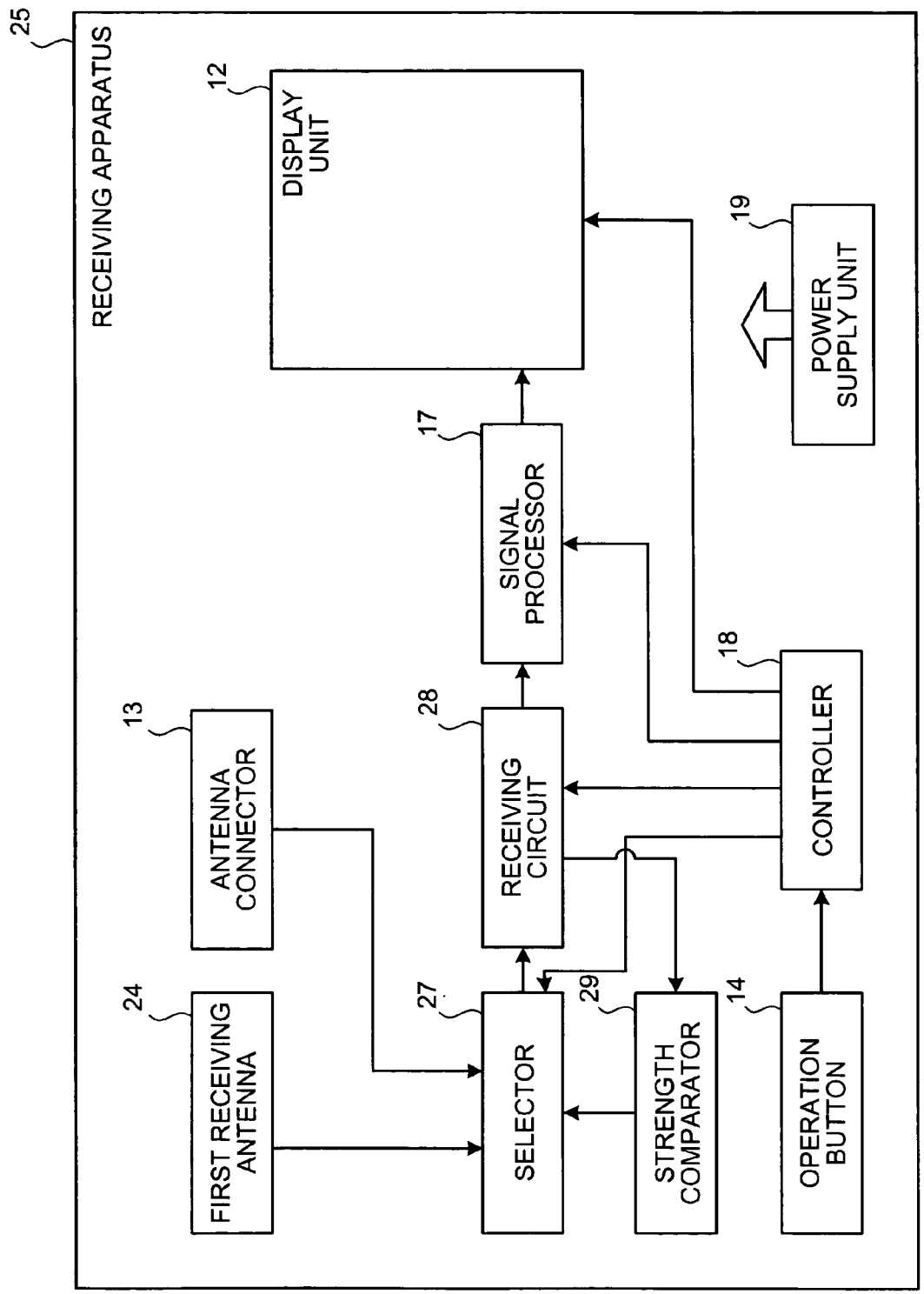
FIG. 6 is a block diagram of a structure of the receiving apparatus provided in the receiving system according to the second embodiment.

FIG. 6 is a schematic block diagram of the receiving apparatus 25 having elements provided in the case member 11. As shown in FIG. 6, the receiving apparatus 25 has the display unit 12, the signal processor 17, and the like that are similar to those of the first embodiment, and in addition, the receiving apparatus 25 has a selector 27, a receiving circuit 28, and a strength comparator 29. The selector 27 outputs one of the radio signals input from the first receiving antenna 24 and the radio signals input from the antenna connector 13. The receiving circuit 28 performs a receiving processing on the radio signals output from the selector 27, and outputs signals indicating strength of the radio signals. The strength comparator 29 compares the strength of the radio signals input from the first receiving antenna 24 and the antenna connector 13 based on the signals indicating the strength of the radio signals obtained by the receiving circuit 28.

The selector 27 serves to select one of the radio signals received through the first receiving antenna 24 and the radio signals received through the antenna connector 13 (the second receiving antenna 2 when the second receiving antenna 2 is connected to the antenna connector 13), and output the selected radio signals. Specifically, the selector 27 selects an antenna that receives the radio signals at higher strength based on a comparison result output from the strength comparator 29, and outputs the radio signals received through the selected antenna to the receiving circuit 28.

The receiving circuit 28 has the functions of the receiving circuit 16 in the first embodiment, and in addition, the receiving circuit 28 generates signals (for example, received signal strength indicator (RSSI)) representing the strength of the input radio signals. Further, the receiving circuit 28 outputs the generated signals to the strength comparator 29.

The strength comparator 29 compares strength of the radio signals based on the signals such as the RSSI output from the receiving circuit 28, and outputs the comparison result to the selector 27. Specifically, as an initial mode, the controller 18 commands the selector 27 to sequentially output the radio signals, which are input from the first receiving antenna 24, and the radio signals, which are input from the antenna connector 13, to the receiving circuit 28. In response to the aforementioned commands, the selector 27 outputs the radio signals input from the first receiving antenna 24 and the antenna connector 13 to the receiving circuit 28, and the receiving circuit 28 outputs the signals corresponding to the strength of each of the radio signals to the strength comparator 29. The strength comparator 29 compares the strength of the radio signals based on the aforementioned signals corresponding to the strength, outputs the comparison result to the selector 27, and the selector 27 performs the antenna selection.

Advantages associated with the receiving system according to the second embodiment is explained. As explained in the first embodiment, during the test before the body insertable device such as the capsule endoscope 21 is inserted into the subject, the operator of the receiving system can easily arrange the receiving system near the capsule endoscope 21, and such arrangement allows the radio signals transmitted from the body insertable device to be received in good condition. Therefore, it is not particularly necessary to provide a high sensitivity antenna as the first receiving antenna 24, and it is not necessary to provide a configuration such as of the second receiving antenna 2 that can be moved independently of the receiving apparatus 25.

In view of the foregoing, in the second embodiment, the first receiving antenna 24 is miniaturized, the first receiving antenna 24 is housed in the case member 11 of the receiving apparatus 25, and the receiving antenna is switched between the first receiving antenna 24 and the second receiving antenna 2 by the selector 27 to receive the radio signals. Unlike the first embodiment, the first receiving antenna 24 is housed in the case member 11, so that the first receiving antenna 24 is connected to the receiving apparatus 25 at any time. However, since the first receiving antenna 24 is arranged inside the case member 11, the operability of the operator of the receiving system does not decrease during the receiving operation of the radio signals using, for example, the second receiving antenna 2.

The receiving system according to the second embodiment has the strength comparator 29 and the selector 27 in the receiving apparatus 25. Hence, the antenna used to receive the radio signals can be switched automatically. As described hereinbefore, the selector 27 switches the radio signals output to the receiving circuit 28 corresponding to the receiving strength of the radio signals. Therefore, before the body insertable device is inserted into the subject, i.e., when the second receiving antenna 2 is not connected to the antenna connector 13, the selector 27 automatically selects the first receiving antenna 24. When the second receiving antenna 2 is connected to the antenna connector 13 after the body insertable device is inserted into the subject, the selector 27 automatically switches the receiving antenna to be selected to the second receiving antenna 2 since the radio signals received through the second receiving antenna 2 has higher strength. As described hereinbefore, the receiving system according to the second embodiment can automatically switch the receiving antenna, so that the operation of the receiving system is simple.

Modification

A modification of the receiving system according to the second embodiment is explained. In the modification, as similar to the second embodiment, the first receiving antenna 24 is housed in the receiving apparatus, and in addition, the connection between the antenna connector 13 and the second receiving antenna 2 is detected to switch the receiving antennas.

Figure 7:
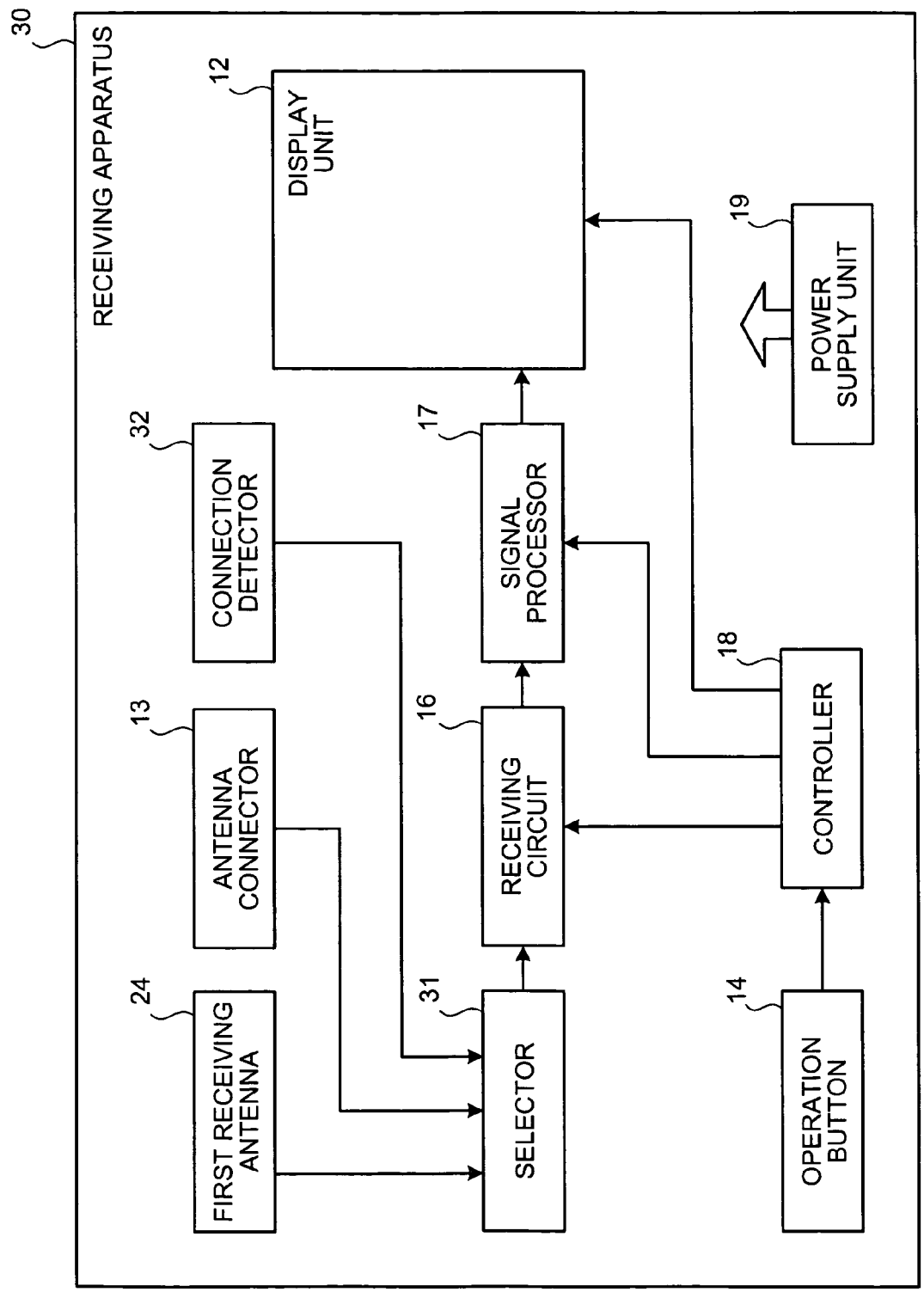
FIG. 7 is a block diagram of a structure of a receiving apparatus according to a modification of the second embodiment.

FIG. 7 is a schematic block diagram of a receiving apparatus 30 according to the modification. As shown in FIG. 7, the receiving apparatus 30 has a connection detector 32, and a detection result of the connection detector 32 is output to a selector 31.

The connection detector 32 detects the connection between the connector 9 provided in the second receiving antenna 2 and the antenna connector 13. Specifically, the connection between the antenna connector 13 and the connector 9 can physically be detected, or electrical conduction between the connector 9 and the antenna connector 13 caused by the connection between the antenna connector 13 and the connector 9 can be detected. The connection detector 32 outputs the detection result to the selector 31, and the selector 31 appropriately switches the receiving antenna to be selected based on the detection result. When the selector 31 acquires the detection result indicating that the second receiving antenna 2 is not connected, the selector 31 always selects the first receiving antenna 24. When the selector 31 acquires the detection result indicating that the second receiving antenna 2 is connected, the selector 31 always selects the second receiving antenna 2. Even when the aforementioned configuration is employed, the receiving system, in which an appropriate receiving antenna is selected without the switching command by the operator, can be realized.

INDUSTRIAL APPLICABILITY

As described hereinbefore, a receiving system according to the present invention is useful for a receiving system that receives radio signals transmitted from a body insertable device inserted into a subject, and particularly, is suitable for a receiving system that receives radio signals transmitted from an capsule endoscope, which is the body insertable device.

The invention claimed is:

1. A receiving system comprising:
a receiving apparatus;
a first receiving antenna that includes;
   a rod-like member having a predetermined rigidity; and
   a first connector which is formed at one end of the rod like member and which serves to connect the first receiving antenna to the receiving apparatus; and
a second receiving antenna that includes;
   a thin and flat shape antenna;
   a second connector for connecting the second receiving antenna and the receiving apparatus; and
   a cable that electrically connects the thin and flat shape antenna and the second connector, wherein
the receiving apparatus includes at least a receiving circuit performing a predetermined receiving processing on radio signal received through one of the first receiving antenna and the second receiving antenna;

before a body insertable device is inserted into a subject, the first receiving antenna receives a first radio signal transmitted from the body insertable device while being arranged near the body insertable device, to determine whether the body insertable device operates normally; and when the body insertable device is inside the subject, the second receiving antenna receives a second radio signal transmitted from the body insertable device, a position of the thin and flat shape antenna being changed to adjust the position and an orientation direction of the thin and flat shape antenna so as to minimize a receiving condition of the second radio signal transmitted from the body insertable device.

2. The receiving system according to claim 1, wherein the receiving apparatus further includes an antenna connector that is electrically connected to the receiving circuit, and allows one of the first receiving antenna and the second receiving antenna to be connected to the receiving apparatus.

3. A receiving system comprising:
a receiving apparatus;
a first receiving antenna; and
a second receiving antenna that includes;
   a thin and flat shape antenna;
   a second connector for connecting the second receiving antenna and the receiving apparatus; and
   a cable that electrically connects the thin and flat shape antenna and the second connector, wherein
wherein the receiving apparatus further includes
   a case member that houses the receiving circuit and the first receiving antenna;
   an antenna connector from which the second receiving antenna is detachable;
   a selector that selects one of the first receiving antenna and the second receiving antenna, and outputs radio signal received through the antenna selected to the receiving circuit; and
   a receiving circuit performing a predetermined receiving processing on radio signal received through one of the first receiving antenna and the second receiving antenna;
before a body insertable device is inserted into a subject, the first receiving antenna receives a first radio signal transmitted from the body insertable device while being arranged near the body insertable device, to determine whether the body insertable device operates normally; and
when the body insertable device is inside the subject, the second receiving antenna receives a second radio signal transmitted from the body insertable device, a position of the thin and flat shape antenna being changed to adjust the position and an orientation direction of the thin and flat shape antenna so as to minimize a receiving condition of the second radio signal transmitted from the body insertable device.

4. The receiving system according to claim 3, wherein the selector selects the antenna based on a strength of the radio signal received through the first receiving antenna and the second receiving antenna.

5. The receiving system according to claim 3, further comprising:
a connection detector that determines whether the second receiving antenna and the antenna connector are connected to each other, wherein the selector selects the first receiving antenna when the connection detector determines that the second receiving antenna and the antenna connector are disconnected from each other, and selects the second receiving antenna when the connection detector determines that the second receiving antenna and the antenna connector are connected to each other.

6. The receiving system according to claim 1, wherein
the second receiving antenna has a member that is deformable according to an external force.

7. The receiving system according to claim 1, further comprising:
a signal processor that extracts subject interior information from a signal including the subject interior information which is transmitted from the body insertable device and processed by the receiving circuit, and
a display unit that displays a content of the subject interior information extracted by the signal processor.

8. The receiving system according to claim 5, wherein the first receiving antenna is connected to the receiving apparatus at any time.

* * * * *